(12) United States Patent
Chung

(10) Patent No.: US 8,325,131 B2
(45) Date of Patent: Dec. 4, 2012

(54) SYSTEM AND METHOD USING MOVEMENT OF HUMAN BODY TO CONTROL A FUNCTION OF A TERMINAL

(75) Inventor: Beom-Su Chung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 816 days.

(21) Appl. No.: 11/476,034

(22) Filed: Jun. 28, 2006

(65) Prior Publication Data

US 2007/0023519 A1 Feb. 1, 2007

(30) Foreign Application Priority Data

Jul. 27, 2005 (KR) ........................ 10-2005-0068604

(51) Int. Cl.
*G09G 5/00* (2006.01)
(52) U.S. Cl. ....... 345/156; 340/4.1; 340/4.11; 340/4.12; 340/4.13; 340/4.14; 463/36
(58) Field of Classification Search ............ 340/825.19, 340/4.1–4.14; 345/156–179; 178/18.01–18.11, 178/19.01–19.07, 20.01–20.04; 463/1–69
See application file for complete search history.

(56) References Cited

U.S. PATENT DOCUMENTS

| | | | | |
|---|---|---|---|---|
| 4,193,061 A | * | 3/1980 | Zoltai | 714/819 |
| 5,131,072 A | * | 7/1992 | Yoshizawa et al. | 706/38 |
| 5,369,731 A | * | 11/1994 | Masumoto et al. | 706/37 |
| 5,474,082 A | * | 12/1995 | Junker | 600/545 |
| 5,638,826 A | * | 6/1997 | Wolpaw et al. | 600/544 |
| 5,692,517 A | * | 12/1997 | Junker | 600/545 |
| 6,493,464 B1 | * | 12/2002 | Hawkins et al. | 382/189 |
| 6,618,712 B1 | * | 9/2003 | Parker et al. | 706/15 |
| 6,989,744 B2 | * | 1/2006 | Proebsting | 340/539.15 |
| 2002/0023265 A1 | * | 2/2002 | Metcalf | 725/74 |
| 2002/0143242 A1 | * | 10/2002 | Nemirovski | 600/300 |

* cited by examiner

*Primary Examiner* — Amare Mengistu
*Assistant Examiner* — Gene W Lee
(74) *Attorney, Agent, or Firm* — H.C. Park & Associates, PLC

(57) ABSTRACT

A system which uses movement of a human body to control a function of a terminal comprises: a detecting device for detecting variation of the movement of the human body depending on an intention of a user so as to transmit a detection signal; and a terminal for storing a reference signal according to at least one class of movement and a control signal corresponding to the reference signal, for searching for a reference signal the same as the detection signal received from the detecting device, and for processing a function based on the control signal corresponding to the reference signal when the reference signal the same as the detection signal is identified. Thereby, a user not only controls the terminal or a driving device, but also performs authentication processing using simple movement of his/her body without any hand operation. A corresponding method for controlling a function using movement of the human body is disclosed.

15 Claims, 10 Drawing Sheets

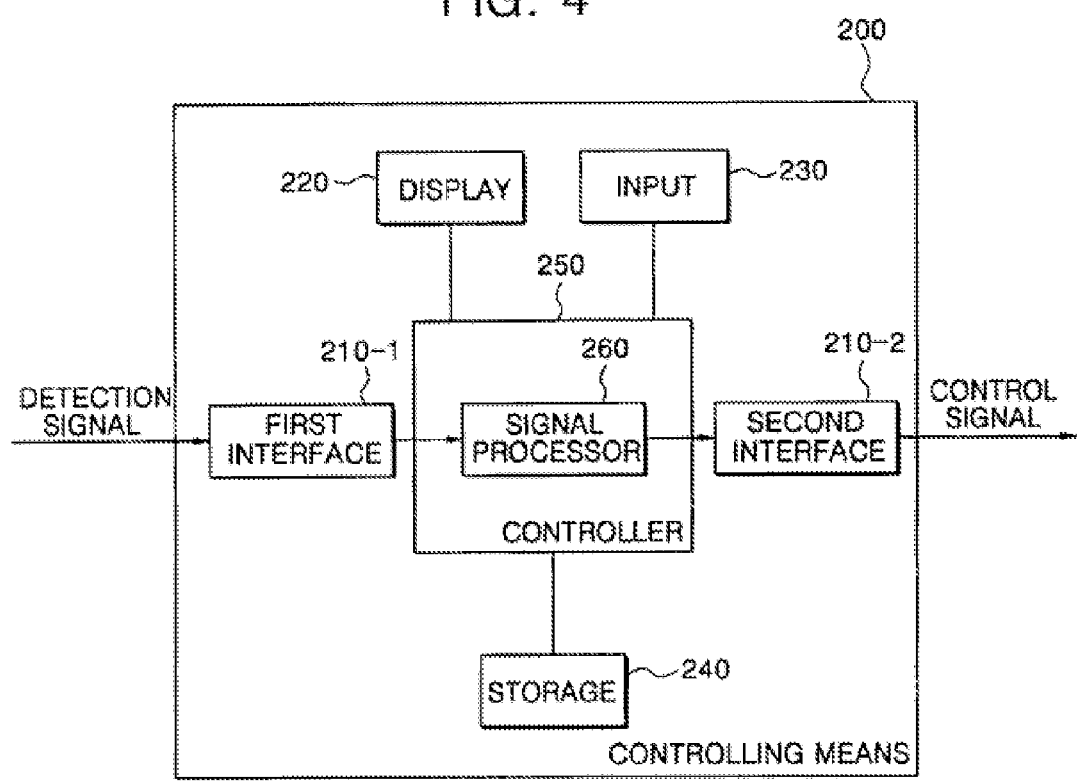

UPWARD

DOWNWARD

LEFTWARD

RIGHTWARD

UPWARD

DOWNWARD

LEFTWARD

RIGHTWARD

SYSTEM AND METHOD USING MOVEMENT OF HUMAN BODY TO CONTROL A FUNCTION OF A TERMINAL

CLAIM OF PRIORITY

This application makes reference to, incorporates the same herein, and claims all benefits accruing under 35 U.S.C. §119 from an application for METHOD AND SYSTEM USING HUMAN BODY MOTION earlier filed in the Korean Intellectual Property Office on Jul. 27, 2005 and there duly assigned Serial No. 10-2005-0068604.

BACKGROUND OF THE INVENTION

1. Technical Field

The present invention relates generally to a system and method using movement of a human body to control a function of a terminal.

2. Related Art

Today, with the development of technology, high-tech terminals such as mobile terminals, game console terminals, etc. take a firm position as the necessities of life.

It is common to these high-tech terminals that a user must directly input a control signal through an external input means (e.g., a remote controller) or a keypad.

For example, when the user intends to perform voice communication with another party through the mobile terminal, the user cannot perform the voice communication until the user selects a phone number or short dialing key button of the other party to then manipulate a communication request button with his/her hand.

However, when simple hand operation is inconvenient, for example, when the user is driving an automobile, has a disabled hand, or is a patient restricted in his/her movements, he/she cannot easily use the high-tech terminal, such as a mobile terminal. Accordingly, the user must receive help from any nearby person in order to use the high-tech terminal.

Thus, a technique designed to allow for use of the high-tech terminal using simple movement of the user's body must be found.

Furthermore, a use authentication procedure for the high-tech terminal has been performed through a simple button combination. However, when simple hand operation is difficult for the user, no technique capable of performing the use authentication procedure has been disclosed. Therefore, the user must be allowed to perform the use authentication procedure of the high-tech terminal through simple movement of his/her body for greater convenience.

SUMMARY OF THE INVENTION

The present invention, therefore, is devised to solve the aforementioned problem. It is an objective of the present invention to provide a system and method which enable movement of a human body of a user to be used in performing use authentication procedure of a terminal, wherein simple movement of the user's body controls a function of the terminal.

According to a first aspect of the present invention for achieving this objective, a system for controlling a terminal using movement of a human body comprises: a detecting device for detecting variation in the movement of the human body depending on an intention of a user to transmit a detection signal; and a terminal for storing a reference signal according to at least one class and a control signal corresponding to the reference signal, for searching for a reference signal corresponding to the detection signal detected by the detecting device, and for processing a function based on the control signal corresponding to the reference signal identified in the search.

In the first aspect of the present invention, the detecting device preferably comprises: a detector for generating the detection signal based on variation of internal pressure of a middle ear, which varies depending on movement of a tongue in an oral cavity of the human body; and a signal transmitter for transmitting the detection signal generated by the detector to the terminal through a network.

In the first aspect of the present invention, the system may further comprise a driving means which is driven by the control signal outputted by the terminal.

In the first aspect of the present invention, the terminal preferably includes: a storage unit for storing the reference signal and the control signal; a controller for extracting the detection signal from signals received from the detecting device based on a preset threshold value, for searching to determine whether or not a reference signal corresponding to the detection signal exists, and for transmitting the control signal corresponding to the reference signal to the driving means when the reference signal corresponding to the detection signal is identified; and at least one interface for receiving the detection signal from the detecting device through a wired or wireless network, and for transmitting the control signal to the driving means.

According to a second aspect of the present invention, a system for authenticating a terminal using movement of a human body comprises: a detecting device for detecting variation in the movement of the human body depending on an intention of a user to transmit a detection signal; and a terminal for storing a first detection signal received according to selection of a user as an authentication signal, for comparing a received second detection signal with the authentication signal to determine whether or not they are identical to each other, and for performing authentication processing.

In the second aspect of the present invention, the terminal may include: a memory for storing the authentication signal; a central processor for storing a first detection signal received according to the selection of the user in the memory as an authentication signal, and for performing the authentication processing according to a result of comparing a received second detection signal with the authentication signal; and a function processor for processing a function according to the selection of the user based on a result of the authentication processing of the central processor.

According to a third aspect of the present invention, a method for controlling a system for controlling a terminal, wherein the system has a detecting device, comprises the steps of: setting at least one reference signal and a control signal depending on movement of a human body; checking a detection signal received from the detecting device depending on movement of the human body; searching for a reference signal which is the same as the detection signal; and transmitting the control signal to the terminal when the reference signal is the same as the detection signal.

In the third aspect of the present invention, the step of searching for a reference signal which is the same as the detection signal may include the sub-steps of: setting a signal received from the detecting device for a predetermined time as a noise signal; and searching for a reference signal which is the same as the detection signal and removing a value of the noise signal from a value of the detection signal.

According to a fourth aspect of the present invention, a method for processing authentication of a system having a detection device and a terminal using movement of a human body comprises the steps of: setting a first detection signal received from the detecting device according to selection of a user as an authentication signal; comparing a second detection signal received from the detecting device with the authentication signal; outputting an authentication failure warning signal when the second detection signal is not identical to the authentication signal; and performing authentication completion processing when the second detection signal is identical to the authentication signal.

In the fourth aspect of the present invention, the method may further comprise the steps of: setting a signal received from the detecting device for a predetermined time as a noise signal; setting a signal, removing a value of the noise signal from a value of the first detection signal, as the authentication signal; and comparing a signal, removing the value of the noise signal from a value of the second detection signal, with the authentication signal.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein:

FIG. 4 is a block diagram for explaining a controlling means according to an exemplary embodiment of the present invention;

DETAILED DESCRIPTION OF THE INVENTION

Hereinafter, a system and method of using a human body motion according to the present invention will be described in more detail with reference to the accompanying drawings.

Figure 1:
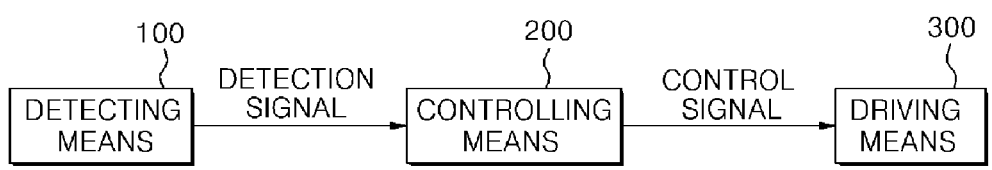
FIG. 1 is a block diagram for explaining a control system according to an exemplary embodiment of the present invention.

FIG. 1 is a block diagram for explaining a control system according to an exemplary embodiment of the present invention.

Referring to FIG. 1, a control system according to the present invention includes a detecting means 100, a controlling means 200 and a driving means 300.

The detecting means 100 comprises a human body response sensor, and transmits a detection signal depending on movement of the human body.

The controlling means 200 generates a control signal based on the detection signal provided by the detecting means 100, and transmits it to the driving means 300.

More specifically, the controlling means 200 extracts at least one detection signal and a control signal, corresponding to a detection signal received after setting a control signal corresponding to each detection signal, and provides the control signal to the driving means 300.

The driving means 300 is driven by the control signal received from the controlling means 200.

The controlling means 200 may be integral with or separate from the driving means 300.

For example, the driving means 300 may include all means that are driven by input of the user, including of a mobile terminal, an electronic wheel chair, a game console and so forth. The following description will be presented using the mobile terminal as an example.

Figure 2:
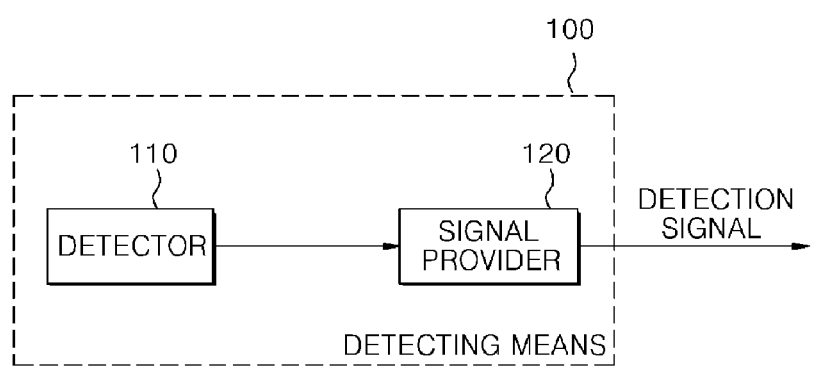
FIG. 2 is a block diagram of a detecting means according to an exemplary embodiment of the present invention.

FIG. 2 is a block diagram of a detecting means according to an exemplary embodiment of the present invention.

Referring to FIG. 2, detecting means 100 according to the present invention includes a detector 110 and a signal provider 120.

The detector 110 may be composed of a pressure sensitive sensor or the like, and detects pressure in a middle ear which varies with movement of a user's body, for example movement in an oral cavity. The detector 110 generates an electrical signal, namely a detection signal, corresponding to the detected pressure.

Furthermore, the signal provider 120 transmits the detection signal, which has been generated by the detector 110 on the basis of the movement of the human body, to the controlling means 200.

The signal provider 120 may be connected with the controlling means 200 through a wired network, such as a cable or a wireless network based on Bluetooth.

Figure 3:
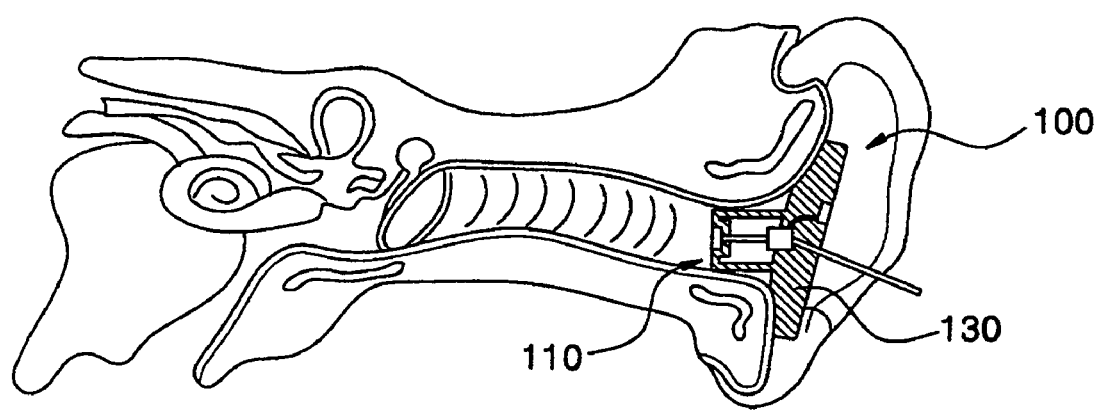
FIG. 3 is a view for explaining a wearing state of a detecting means according to an exemplary embodiment of the present invention.

FIG. 3 is a view for explaining a wearing state of a detecting means according to an exemplary embodiment of the present invention.

As shown in FIG. 3, according to the present invention, detecting means 100 is brought into close contact with an external ear of the human body, thereby being capable of minimizing a signal received from the exterior of the human body and detecting pressure in the middle ear with precision.

To be specific, the detecting means 100 includes a signal breaker 130 having an internal shape similar to an external shape of the external ear, thereby preventing an external signal from being inputted into the middle ear, as well as preventing an internal pressure of the middle ear from being varied by an external pressure.

Furthermore, the pressure sensitive sensor used for the detector 110 is mounted on an inner surface of the signal breaker 130, thereby detecting variation of the internal pressure of the middle ear with precision.

Specifically, when any person talks or moves his/her tongue, namely when a tongue moves in the oral cavity, an air flow in the middle ear communicating with the oral cavity is varied, and thus the internal pressure of the middle ear varies. A detection signal, dependent on the variation of the internal pressure of the middle ear, is transmitted to the controlling means 200 by the detecting means 100.

FIG. 4 is a block diagram for explaining a controlling means 200 according to an exemplary embodiment of the present invention.

Referring to FIG. 4, controlling means 200 includes a plurality of interfaces 210-1 and 210-2, a display 220, an input 230, a storage 240 and a controller 250, wherein the controller 250 includes a signal processor 260.

The first interface 210-1 receives a detection signal from detecting means 100, and transmits it to the controller 250.

At this point, the first interface 210-1 receives the detection signal from the detecting means 100 through a wired or wireless network.

The second interface 210-2 transmits a control signal corresponding to the detection signal to driving means 300 through the wired or wireless network.

In order to prevent signals exchanged by each interface from overlapping with the other, when the first interface 210-1 is connected to the detecting means 100 over a wired network, the second interface 210-2 is preferably connected to the driving means 300 over a wireless network.

The input 230 provides the controller 250 with an input signal inputted by the user. In other words, the input 230 sets a control signal corresponding to the detection signal received from the detecting means according to the input of the user.

The display 220 outputs display and voice information which are set by a display signal received from the controller 250. The display and voice information outputted by the display 220 may include information which displays the detection signal received from the detecting means 100 or the control signal transmitted by the controlling means 200.

The storage 240 stores at least one detection signal received from the detecting means 100 and the control signal corresponding to each detection signal.

When the controlling means 200 is connected to a mobile terminal, the control signal stored in the storage 240 may correspond to a short dialing button signal or a specified key button signal. Furthermore, when the controlling means 200 is connected to an electronic wheel chair, the control signal stored in the storage 240 may correspond to a speed button signal or a direction button signal.

The controller 250 stores the control signal, which corresponds to each detection signal inputted through the input 230, in the storage 240. Furthermore, the controller 250 extracts the control signal corresponding to the detection signal received from the detecting means 100, and transmits it to the driving means 300.

The signal processor 260 of the controller 250 monitors variation of the signal received from the detecting means 100 to determine start and end points of the detection signal received from the detecting means 100.

FIGS. 5A to 5D are time-to-frequency graphs for explaining results of measuring variation of an internal pressure of a middle ear as applied to the present invention.

Figure 5A:
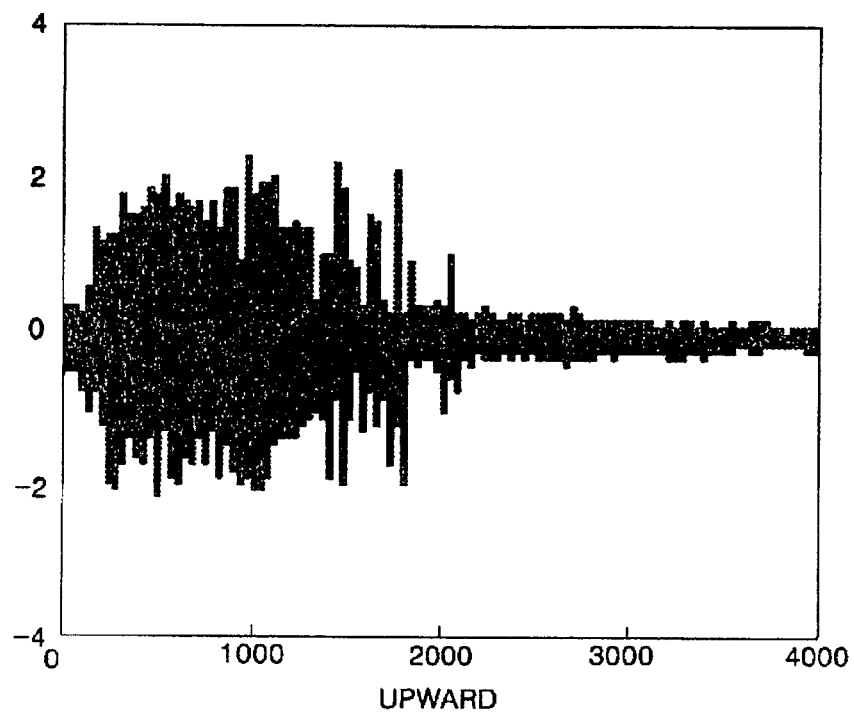
FIGS. 5A to 5D are time-to-frequency graphs for explaining results of measuring variation of an internal pressure of a middle ear as applied to the present invention.
Figure 5B:
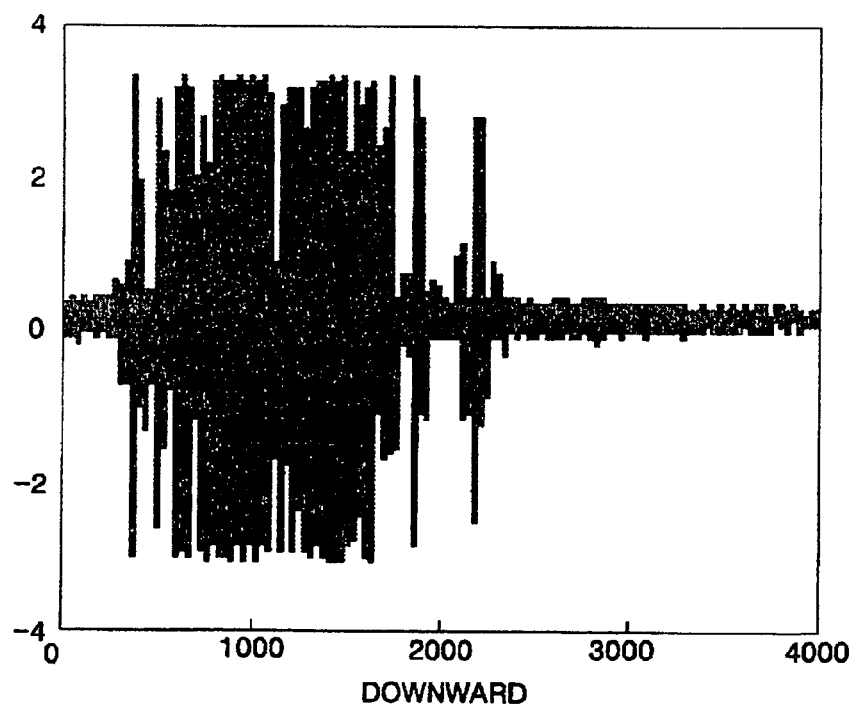

Referring to FIGS. 5A to 5D, when a tongue in an oral cavity moves upward, values measuring variation of the internal pressure of the middle ear are as shown in FIG. 5A. Furthermore, when the tongue in the oral cavity moves downward, values measuring variation of the internal pressure of the middle ear are as shown in FIG. 5B.

Figure 5C:
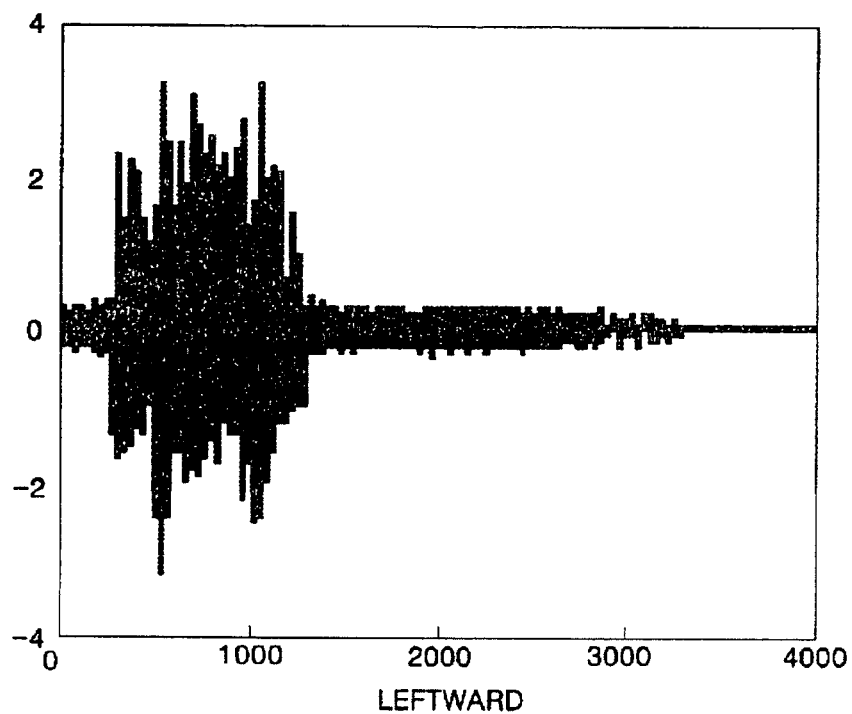
Figure 5D:
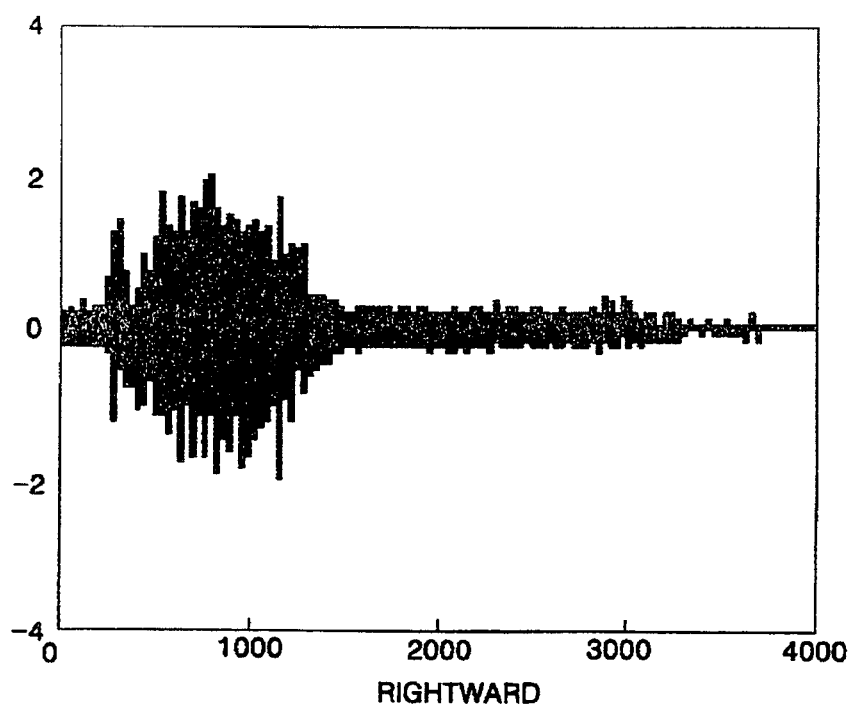

When the tongue in the oral cavity moves leftward, values measuring variation of the internal pressure of the middle ear are as shown in FIG. 5C, and when the tongue in the oral cavity moves rightward, values measuring variation of the internal pressure of the middle ear are as shown in FIG. 5D.

As shown in FIGS. 5A to 5D, the variation of the internal pressure of the middle ear varies depending on the movement of tongue in the oral cavity, and has a characteristic result value.

In order to use, as a reference signal, the values measuring the variation of the internal pressure of the middle ear having the characteristic result value, appropriate threshold processing is required.

In other words, the detecting means 100 differentiates among a value measuring pressure detected when the tongue does not move, a value measuring pressure detected when the tongue begins to move, and a value measuring pressure detected when the tongue stops moving. For the purpose of the differentiation, threshold processing is required.

A threshold value required for this threshold processing is found as follows.

Variations of the internal pressure of the middle ear in connection with the upward movement (first class), downward movement (second class), leftward movement (third class) and rightward movement (fourth class) of the tongue are measured at least once so as to determine the measured values.

An average value of the values (energy values) squaring signal values (amplitudes) of the measured values of the respective classes is yielded.

A maximum measured signal value of the class having the minimum average value of the average values of the respective classes is multiplied by any one of the values from 0.6 to 0.9, and the resultant value is selected as the threshold value.

Figure 6:
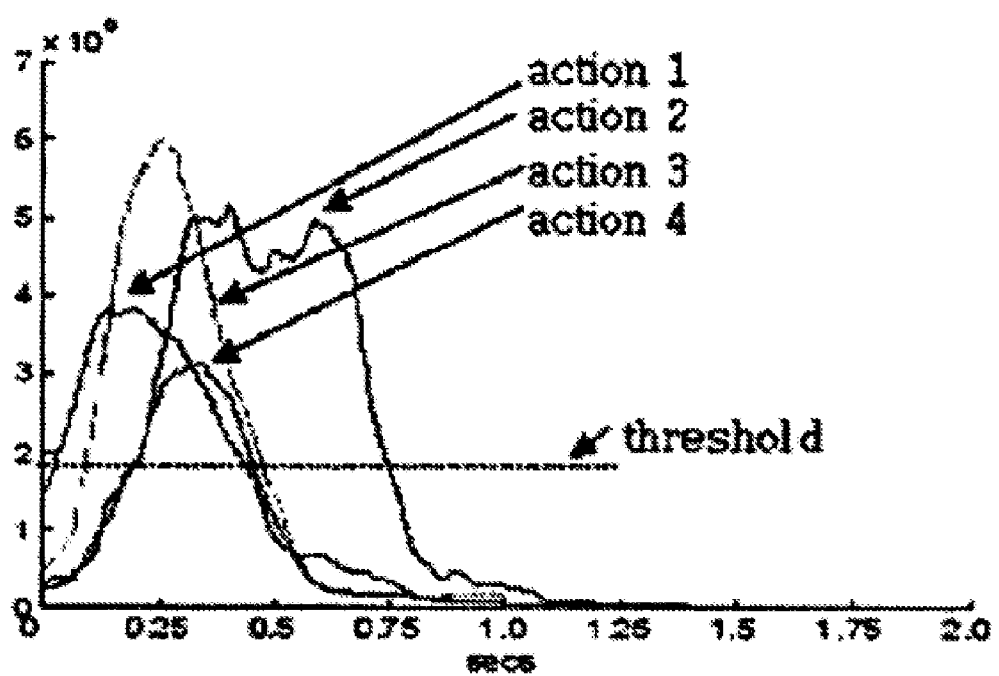
FIG. 6 is a view for explaining a threshold value according to the present invention.
Figure 7A:
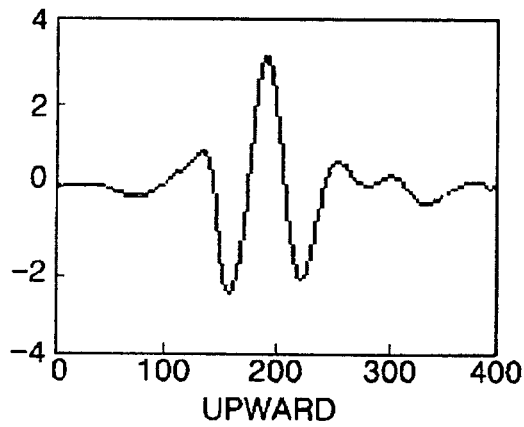
FIGS. 7A to 7D are graphs for explaining a characteristic detection signal of each class applied to the present invention.
Figure 7B:
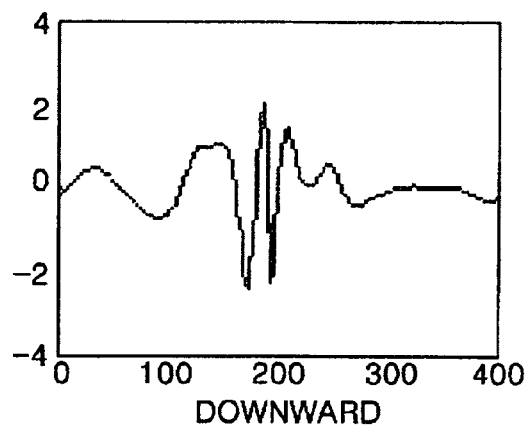
Figure 7C:
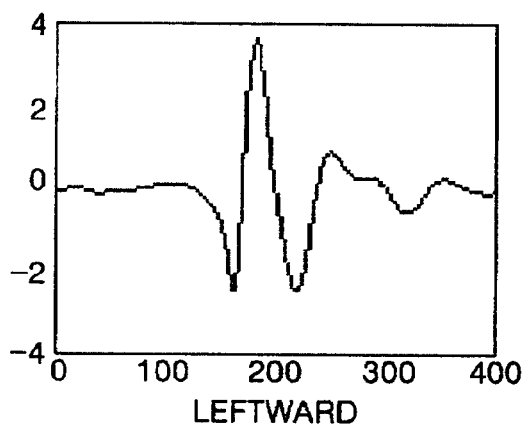
Figure 7D:
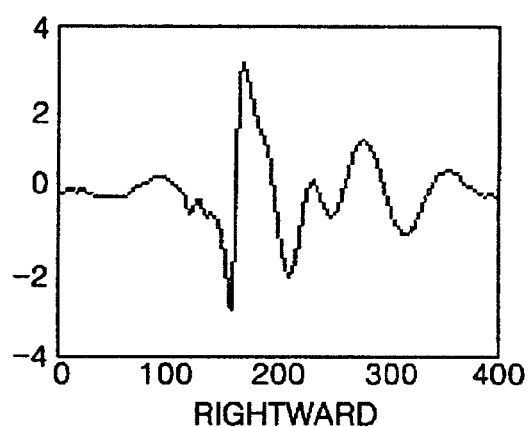

FIG. 6 is a graph for explaining a threshold value according to the present invention.

As shown in FIG. 6, when the maximum measured signal value of the class having the minimum average value of the average values of the respective classes is multiplied by any one of the values from 0.6 to 0.9, the resultant product is selected as the threshold value, and it is possible to determine start and end points of the value measuring the variation of the internal pressure of the middle ear according to each class, namely start and end points of the detection signal.

Meanwhile, in order to determine the detection signals received from the detecting means on the basis of each class, the value resulting from measuring the variation of the internal pressure of the middle ear according to each class is repeatedly collected from an individual user, and then an average value of the collected values is computed.

Furthermore, in order to differentiate the detection signals received from the detecting means 100 on the basis of each class, the detection signal is extracted from signals received from the detecting means 100 using the threshold value and a predetermined size of window (e.g., 400). At this point, the window size of "400" is a size selected as a test result for differentiating the detection signals according to movements of class-specific users.

An energy value (a square value of 400 signals) of a signal corresponding to a signal of the window size, which is selected from the signals received from the detecting means 100, is obtained. If the energy value is greater than the threshold value and has a predetermined duration, it is determined as the start point of the detection signal. In contrast, if the energy value is less than the threshold value, it is determined to be the end point of the detection signal.

When a "center of mass" theory is applied to the detection signal received from the detecting means 100, the characteristic detection signal of each class depending on the variation of the internal pressure of the middle ear, caused by minute movement of the tongue, is obtained.

FIGS. 7A to 7D are graphs for explaining a characteristic detection signal of each class applied to the present invention.

Referring to FIGS. 7A to 7D, it can be found that an average value of the values resulting from measuring the variation of the internal pressure of the middle ear for a large number of persons has a characteristic signal value according to each class.

Thus, while monitoring signals received from the detecting means 100, the controlling means 200 selects a time point of receiving a detection signal greater than a threshold value as a start point, and a time point of receiving a detection signal less than a threshold value as an end point. Thereby, the controlling means 200 extracts a control signal corresponding to the detection signal received from the start point to the end point.

Furthermore, in order to yield a reference signal used to differentiate the detection signals received from the detecting means according to each class, a pairwise cross correlation average method can be used. Because each person has his/her own force, speed, etc. of moving his/her own tongue, it is difficult to yield the exact reference signal capable of determining each class using a typical method of obtaining the average value.

Accordingly, in order to obtain the reference signal, the detection signals collected previously according to each class are formed in pairs, and are then aligned through cross correlation to the utmost extent. An average signal of each corresponding pair of detection signals is calculated using the pairwise cross correlation average method, and an average signal of each calculated pair of average signals is calculated again. These processes are repeatedly performed. As a result, the finally calculated average signal is selected as the reference signal of each class.

Figure 8:
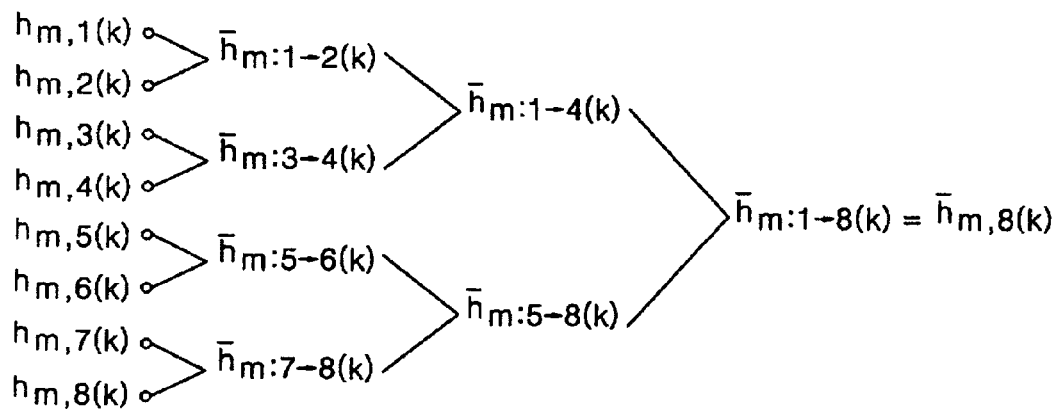
FIG. 8 shows a function of yielding a reference signal according to the present invention.

FIG. 8 shows a function of yielding a reference signal according to the present invention.

As shown in FIG. 8, the process of obtaining an average value after pairing detection signal values of each class and aligning the paired values through cross correlation is repeated, and thereby a reference signal can be yielded.

The reference signal according to each class and a control signal corresponding to each reference signal inputted from the input 230 are stored in the storage 240.

The signal processor 260 of the controller 250 determines start and end points of the detection signal based on a threshold value while monitoring signals received from the detecting means 100.

Furthermore, the signal processor 260 searches for a reference signal the same as the detection signal among the reference signals stored in the storage 240.

At this point, the signal processor 260 can search for the reference signal by applying a predetermined tolerance 500 to a value of the detection signal. In other words, because the force or speed of moving the tongue is not constant, the signal processor 260 preferably applies the predetermined tolerance 500 to the value of the received detection signal to search for a similar reference signal, even when the reference signal has the predetermined tolerance 500 with respect to the value of the detection signal.

Furthermore, the signal processor 260 sets a signal, which is received from the detecting means 100 for a predetermined time in a state where there is no movement of the tongue in the oral cavity, as a noise signal. Then, the signal processor 260 removes the noise signal from the detection signal received from the detecting means 100, and then searches for a reference signal the same as the detection signal.

The following Tables 1 and 2 show test result values which the controlling means of the present invention uses to search for a reference signal according to a detection signal received from the detecting means 100 in a percentage (%) unit.

Table 1

TABLE 1

|  | First control signal | Second control signal | Third control signal | Fourth control signal |
| --- | --- | --- | --- | --- |
| First reference signal | 100 | 0 | 0 | 0 |
| Second reference signal | 0.14 | 98.94 | 0.17 | 0.74 |
| Third reference signal | 0 | 0 | 100 | 0 |
| Fourth reference signal | 1.89 | 0.09 | 1.11 | 96.91 |

Table 2

TABLE 2

|  | First control signal | Second control signal | Third control signal | Fourth control signal |
| --- | --- | --- | --- | --- |
| First reference signal | 100 | 0 | 0 | 0 |
| Second reference signal | 0 | 99.09 | 0.91 | 0 |
| Third reference signal | 0 | 0 | 100 | 0 |
| Fourth reference signal | 0.74 | 0.29 | 1.29 | 97.96 |

As seen from Tables 1 and 2, the controlling means 200 searches for a reference signal the same as the detection signal received from the detecting means 100 according to each class, and then each of the control signals which the controlling means 200 transmits to the driving means 300 is an independent result value. Therefore, the user can select the control signal transmitted to the driving means 300 by movement of the tongue in the oral cavity according to each class.

The signal processor 260 transmits the control signal corresponding to the searched reference signal to the driving means 300. Thereby, operation of the driving means 300 is adapted to be controlled according to the movement of the human body.

Meanwhile, when a control signal corresponding to the received reference signal is not identified, the signal processor 260 outputs a warning signal through the display 220 after a predetermined time has elapsed so as to cause the user to move his/her body again.

Figure 9:
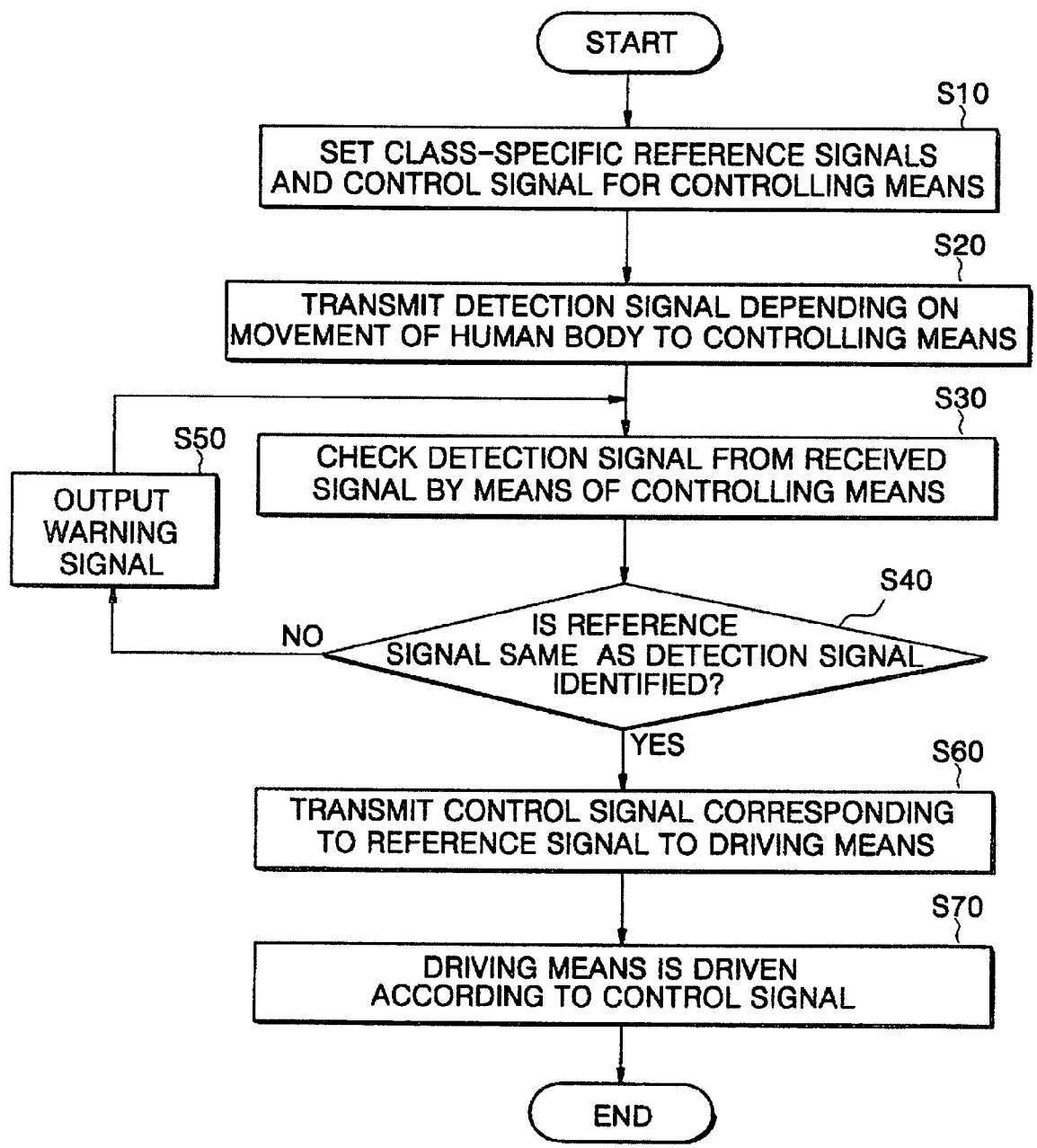
FIG. 9 is a flow chart for explaining a method of performing control using movement of a human body according to an exemplary embodiment of the present invention.

FIG. 9 is a flow chart for explaining a method of performing control using movement of a human body according to an exemplary embodiment of the present invention.

Referring to FIG. 9, a user sets a reference signal according to each class and a control signal corresponding to each reference signal for the controlling means 200 (S10).

Then, the detecting means 100 transmits a detection signal according to movement of a human body, to the controlling means 200 (S20).

In one example, the detecting means 100 detects variation of internal pressure of the middle ear according to movement of a tongue in an oral cavity of the human body, and transmits it to the controlling means 200.

The controlling means 200 determines start and end points of the detection signal depending on a threshold value while monitoring signals received from the detecting means 100 (S30).

Subsequently, the controlling means 200 searches for a reference signal the same as the detection signal (S40).

At this point, the controlling means 200 searches the reference signal by applying a predetermined tolerance 500 to a value of the detection signal.

If a reference signal the same as the detection signal is not identified for a predetermined time, the controlling means 200 outputs a warning signal reporting that the movement of the human body is not properly recognized so as to cause the user to move his/her body again (S50). Then, the controlling means 200 determines the start and end points of the detection signal received from the detecting means 100 according to movement of the tongue (S30).

Meanwhile, if a reference signal the same as the detection signal is identified, the controlling means 200 transmits the control signal corresponding to the reference signal to the driving means 300 (S60).

In one example, when the driving means 300 is a mobile terminal and the controlling means 200 is included in the mobile terminal, the controlling means 200 generates a hot key control signal corresponding to the detection signal so as to cause the mobile terminal to process a function related to the hot key control signal.

At this point, the hot key control signal may include a short dialing control signal, short dialing button control signal, or a specified (e.g., conversation or end) button control signal.

The driving means 300 (mobile terminal) may generate a call request message according to the received hot key control signal, it may set a conversation mode, or it may terminate a conversation call.

Meanwhile, if the driving means 300 is a means for operating an electronic wheel chair of the like, the controlling means 200 transmits a direction or speed control signal corresponding to the detection signal to the driving means 300, and then the driving means 300 accelerates/decelerates a speed or changes a direction of the electronic wheel chairs on the basis of the received control signal (S70).

Figure 10:
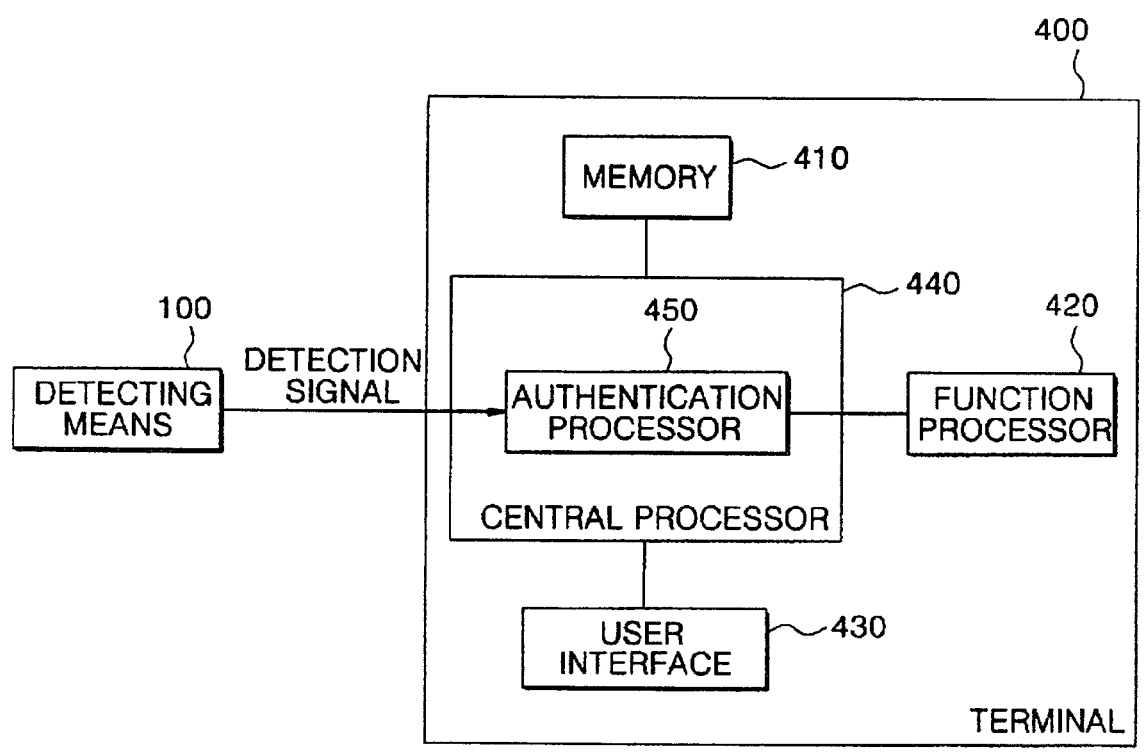
FIG. 10 is a block diagram for explaining an authentication system according to another exemplary embodiment of the present invention.

FIG. 10 is a block diagram for explaining an authentication system according to another exemplary embodiment of the present invention.

Referring to FIG. 10, a control system according to another embodiment of the present invention includes a detecting means 100 and a terminal 400.

The detecting means 100 provides a detection signal according to movement of a human body, and is connected with the terminal 400 through a wired or wireless network.

The terminal 400 includes a central processor 440, a function processor 420, a memory 410 and a user interface 430, wherein the central processor 440 has an authentication processor 450.

The user interface 430 may have a plurality of selection fields (not shown) and display means (not shown). The user interface 430 provides a selection signal according to the selection of a user, or displays a detection signal received from the detecting means 100 according to a display signal received from the central processor 440, information on a state of the terminal 400, and so forth.

The function processor 420 provides functions inherent in the terminal 400. For example, when the terminal 400 is a mobile terminal, the function processor 420 provides a voice communication service according to a phone number which the user inputs, or an Internet service over a communication network. When the terminal 400 is an electronic wheel chair, the function processor 420 provides a driving function of the chair.

The selection provided by the user interface 430 includes an authentication setup signal for setting an initial authentication signal, an authentication request signal for requesting an authentication procedure, a completion processing signal for requesting function processing according to completion of the authentication procedure, and a function request signal for requesting a function of the terminal 400.

When the authentication setup signal is received from the user interface 430, the central processor 440 stores a detection signal received from the detecting means 100 for a predetermined time in the memory 410 as an authentication signal.

Because of differences in the oral cavities of various users, and in the force or speed of each user moving his/her tongue, when the internal pressure of the middle ear which varies with the movement of the tongue of each user and is measured, each user has a characteristic result value. Therefore, the result value measuring variation of the internal pressure of the middle ear depending on the movement of the tongue in the oral cavity can be used as characteristic authentication information.

When the authentication request signal is received, the central processor 440 determines whether or not the detection signal received from the detecting means 100 is identical to the authentication signal stored in the memory 410. If so, the central processor 440 allows the user to control the function processor 420 through the user interface 430.

Specifically, the authentication processor 450 of the central processor 440 determines start and end points of the detection signal according to a threshold value while monitoring detection signals received from the detecting means 100 in a state where the authentication setup signal is received, and stores the detection signal in the memory 410 as the authentication signal.

When the authentication request signal is received, the authentication processor 450 determines whether or not the detection signal received from the detecting means 100 is identical to the authentication signal stored in the memory 410.

If the detection signal is not identical to the authentication signal, the authentication processor 450 outputs a warning signal to inform the user that the authentication procedure is not completed. Thus, when the warning signal is outputted by the terminal 400, the authentication procedure based on the movement of the user body is performed again.

If the detection signal is identical to the authentication signal and when the authentication completion signal is received, the authentication processor 450 transmits an authentication acknowledgment signal to the function processor 420 so as to cause the function processor 420 to process the function according to the function request signal received from the user interface 430.

At this point, the authentication processor 450 applies a predetermined tolerance 500 to a value of the detection signal to determine whether or not the detection signal is identical to the authentication signal.

Furthermore, the authentication processor 450 sets the signal received from the detecting means 100 for a predetermined time as a noise signal, and then removes the noise signal from the signal received from the detecting means. Preferably, the authentication processor 450 then stores the authentication signal in the memory 410, and compares the signal after removal with the authentication signal.

Therefore, the user can use the terminal 400 to perform the authentication procedure using the movement of his/her body after setting the movement of his/her body as authentication information.

Figure 11:
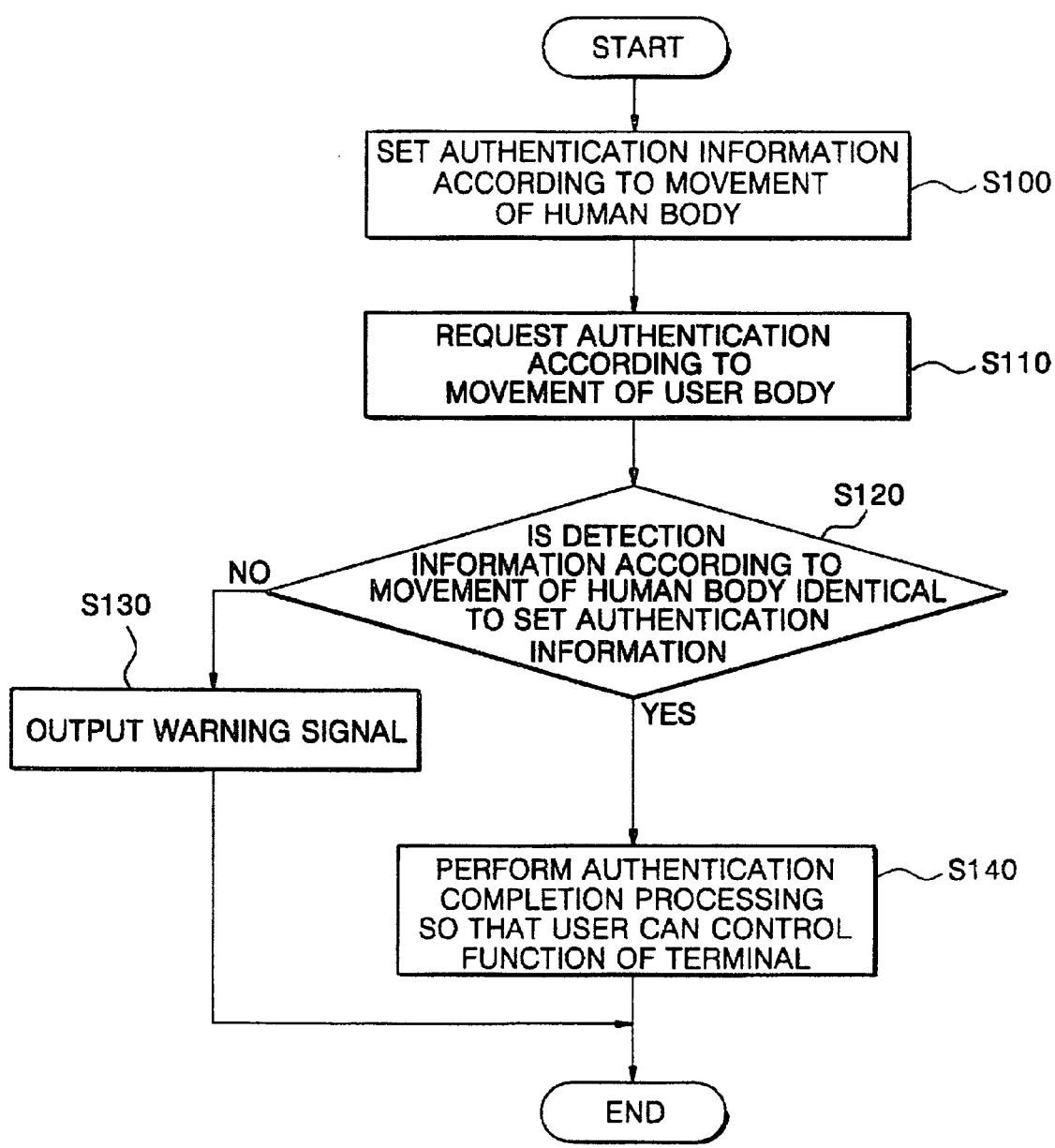
FIG. 11 is a flow chart for explaining a method of performing authentication processing using movement of a human body in accordance with another embodiment of the present invention

FIG. 11 is a flow chart for explaining a method of performing authentication processing using movement of a human body in accordance with another embodiment of the present invention.

FIG. 11, a user sets up authentication information for the terminal 400 according to movement of his/her body (S100).

At this point, the user can set up/change the authentication information in initially or subsequently using the terminal 400 at his/her option.

In one example, the user can set a detection signal of at least one class as authentication information in the terminal 400 according to movement of the tongue in his/her oral cavity.

The user makes an authentication request through the user interface 430 when intending to use a function of the terminal 400, and moves the tongue in his/her oral cavity according to the class set as the authentication information (S100).

The detecting means 100 detects variation of the internal pressure of the middle ear depending on the movement of the tongue in his/her oral cavity, and transmits the detection signal to the terminal 400. The terminal 400 determines start and end points of the detection signal according to a threshold value while monitoring signals received from the detecting means 100.

The terminal 400 determines whether the received detection signal is identical to the authentication signal (S120).

When the detection signal of at least one class is set for the terminal 400 as the authentication signal, the user sequentially moves his/her body corresponding to the class, and the terminal 400 determines whether or not the detection signals received sequentially are identical to the respective authentication signals.

At this point, the terminal 400 applies a predetermined tolerance 500 to a value of the detection signal, and determines whether or not the received detection signal is identical to the authentication signal.

If the received detection signal is not identical to the authentication signal, the terminal 400 outputs a warning signal reporting that the authentication procedure is not completed so as to cause the user to repeat the authentication procedure (S130).

Conversely, if the received detection signal is identical to the authentication signal, the terminal 400 completes the authentication procedure so as to cause the user to control the function of the terminal 400 through the user interface 430 (S140).

In one example, the authentication processor 450 of the terminal 400 transmits an authentication acknowledgment signal to the function processor 420 when the detection signal received from the detection means 100 is identical to the set authentication signal so as to cause the function processor 420 to be driven according to a function request signal which the user inputs through the user interface 430.

While the above-mentioned description of the present invention has been made regarding the case of performing the authentication procedure or providing a corresponding control signal based on the variation of the internal pressure of the middle ear in dependence upon the movement of the tongue of the oral cavity of the human body, it can be equally applied to the case where a characteristic detection signal dependent upon another movement of the human body is generated.

Furthermore, while the above-mentioned description of the present invention has been made with reference to terminal 400 performing the authentication procedure based on the movement of the human body as one example, the invention can be applied to all apparatuses for performing an authentication procedure, such as another locking safety apparatus.

As can be seen from the foregoing, any user can control the terminal 400 or driving means 300 intended for use using minute movement of his/her body.

Furthermore, the user can perform the authentication procedure for use based on the movement of his/her body.

Although exemplary embodiments of the present invention have been described, it will be understood by those skilled in the art that the present invention should not be limited to the described exemplary embodiments. Rather, various changes and modifications can be made within the spirit and scope of the present invention, as defined by the following claims.

What is claimed is:

1. A system for controlling a terminal using movement of a human body, the system comprising:
   a detecting device to transmit a detection signal corresponding to variation detected in the movement of the human body; and
   a terminal to store a reference signal according to at least one class of movement and a control signal corresponding to the reference signal, to determine whether the detection signal is substantially identical to the reference signal, and, in response to a determination that the detection signal is substantially identical to the reference signal, to transmit the control signal corresponding to the reference signal,
   wherein the reference signal is selected based on an average of at least two detection signals using a pairwise cross correlation average method.

2. The system of claim 1, wherein the detecting device comprises:
   a detector to generate the detection signal based on variation of an internal pressure of a middle ear dependent on movement of a tongue in an oral cavity of the human body; and
   a signal transmitter to transmit the detection signal generated by the detector to the terminal through a network.

3. The system of claim 2, wherein the detecting device further comprises a signal breaker having an internal shape the same as an external shape of an external ear of the human body, the signal breaker being configured to prevent variation of an external pressure from exerting an influence on the variation of the internal pressure of the middle ear.

4. The system of claim 1, further comprising a driver responsive to the control signal for carrying out the function.

5. The system of claim 4, wherein the terminal comprises:
   a storage to store the reference signal and the control signal;
   a controller to extract the detection signal from among signals received from the detecting device based on a threshold value, to determine whether the detection signal is substantially identical to the reference signal, and, in response to the determination that the detection signal is substantially identical to the reference signal, to transmit the control signal corresponding to the reference signal to the driver; and
   at least one interface to receive the detection signal from the detecting device through at least one of a wired network and a wireless network, and to transmit the control signal to the driver.

6. The system of claim 5, wherein the threshold value comprises a value corresponding to a minimum detection signal among the detection signals generated dependent upon at least one movement of the human body.

7. The system of claim 1, wherein the terminal is configured to set a signal received from the detecting device for a predetermined time as a noise signal, to remove the noise signal from the detection signal, and to determine whether the reference signal is substantially identical to the detection signal having the noise signal removed.

8. The system of claim 1, wherein the terminal is configured to compare a value of the detection signal to a value of the reference signal, and, in response to a determination that the difference between the value of the detection signal and the value of the reference signal is within a set tolerance, to determine that the detection signal is substantially identical to the reference signal.

9. A method for controlling a system for controlling a terminal, the system having a detecting device, the method comprising:
   storing a reference signal according to at least one class of movement and a control signal corresponding to the reference signal;
   receiving a detection signal from the detecting device, the detection signal corresponding to variation detected in the movement of a human body;
   determining whether the detection signal is substantially identical to the reference signal; and
   transmitting, to the terminal, the control signal corresponding to the reference signal,
   wherein the reference signal is selected based on an average of at least two detection signals using a pairwise cross correlation average method.

10. The method of claim 9, wherein receiving the detection signal comprises identifying the detection signal from among signals received from the detecting device based on a threshold value.

11. The method of claim 9, wherein determining whether the detection signal is substantially identical to the reference signal comprises:
   setting a signal received from the detecting device for a predetermined time as a noise signal;
   removing the noise signal from the detection signal; and
   determining whether the reference signal is substantially identical to the detection signal having the noise signal removed.

12. The method of claim 9, wherein determining whether the detection signal is substantially identical to the reference signal comprises comparing a value of the detection signal to a value of the reference signal, and, in response to a determination that the difference between the value of the detection signal and the value of the reference signal is within a set tolerance, to determine that the detection signal is substantially identical to the reference signal.

13. The method of claim 9, wherein the detection signal is generated based on variation of an internal pressure of a middle ear dependent on movement of a tongue in an oral cavity of the human body.

14. The method of claim 9, wherein each of the reference signal, the control signal, and the detection signal is transmitted through at least one of a wired network and a wireless network.

15. The method of claim 9, wherein determining whether the detection signal is substantially identical to the reference signal comprises applying a tolerance to a value of the detection signal.

* * * * *